United States Patent [19]

Tarnowski et al.

[11] Patent Number: 5,202,239
[45] Date of Patent: Apr. 13, 1993

[54] EXPRESSION OF RECOMBINANT POLYPEPTIDES WITH IMPROVED PURIFICATION

[75] Inventors: S. Joseph Tarnowski, Sunnyvale; Sandra Hilliker, Riverside; W. Scott Willett, San Francisco, all of Calif.

[73] Assignee: Scios Nova Inc., Mountain View, Calif.

[21] Appl. No.: 564,259

[22] Filed: Aug. 7, 1990

[51] Int. Cl.$^5$ .................... C12N 15/62; C12N 15/12
[52] U.S. Cl. ..................... 435/69.7; 435/172.3; 435/252.3; 435/320.1; 530/350; 530/412
[58] Field of Search .................. 435/69.7, 172.3; 530/350, 412; 935/47

[56] References Cited

U.S. PATENT DOCUMENTS

| | | | |
|---|---|---|---|
| 4,431,739 | 2/1984 | Riggs | 435/253 |
| 4,532,207 | 7/1985 | Brewer et al. | 435/69.4 |
| 4,743,679 | 5/1988 | Cohen et al. | 530/350 |
| 4,764,504 | 8/1988 | Johnson et al. | 514/12 |
| 4,880,911 | 11/1989 | Brewer et al. | 530/351 |
| 4,897,348 | 1/1990 | Johnson et al. | 435/69.1 |
| 4,987,070 | 1/1991 | Magota et al. | 435/69.7 |

FOREIGN PATENT DOCUMENTS 0163406 12/1985 European Pat. Off. .
0207044 12/1986 European Pat. Off. .
2180539 4/1987 United Kingdom .

OTHER PUBLICATIONS

Bailey et al., *J. Indust. Microbiol.* (1987) 2:47-52.
Sung et al., *Proc. Natl. Acad. Sci.* (1986) 83:561-565.
Cockle et al., "Protein Purification: Micro to Macro" (1987) Alan R. Liss, Inc., pp. 375-381.
Sassenfeld et al., *Bio/Technology* (Jan. 1984) pp. 76-81.

*Primary Examiner*—Garnette D. Draper
*Assistant Examiner*—John D. Ulm
*Attorney, Agent, or Firm*—Morrison & Foerster

[57] ABSTRACT

An improved method for expressing peptides as fusion proteins, uses a carrier for a heterologous peptide to provide a fusion protein having a high pI. The high isoelectric point facilitates separation of the fusion protein from all other host cell proteins, and separation of the carrier from the peptide after cleavage.

8 Claims, 10 Drawing Sheets

```
                                                                    Staph V8
                                                                       ↓
    Met Thr Met Ile Thr Asn Leu Thr Thr Thr Thr Thr Glu Phe Arg
CAT ATG ACC ATG ATT ACG AAT TTA ACC ACC ACC ACC ACC GAA TTC CGT
GTA TAC TGG TAC TAA TGC TTA AAT TGG TGG TGG TGG TGG CTT AAG GCA Met Asn Pro Met Tyr Asn Ala Val Ser Asn Ala Asp Leu Met Asp Phe
ATG AAC CCG ATG TAC AAC GCA GTG TCC AAC GCA GAC CTG ATG GAT TTC
TAC TTG GGC TAC ATG TTG CGT CAC AGG TTG CGT CTG GAC TAC CTA AAG Lys Asn Leu Leu Asp His Leu Gln Gln Lys Met Pro Leu Gln Asp Gln
AAG AAC CTG CTG GAC CAC CTG CAG CAG AAG ATG CCG CTG CAG GAT CAG
TTC TTG GAC GAC CTG GTG GAC GTC GTC TTC TAC GGC GAC GTC CTA GTC Val Val Pro Pro Gln Val Leu Ser Gln Pro Asn Gln Gln Ala Gly Ala
GTT GTG CCG CCG CAG GTT CTG TCT CAA CCG AAC CAG CAG GCT GGT GCT
CAA CAC GGC GGC GTC CAA GAC AGA GTT GGC TTG GTC GTC CGA CCA CGA Ala Leu Ser Pro Leu Pro Gln Val Pro Pro Trp Thr Gly Gln Val Ser
GCT CTG TCT CCG CTG CCG CAG GTT CCG CCG TGG ACC GGT CAG GTT TCT
CGA GAC AGA GGC GAC GGC GTC CAA GGC GGC ACC TGG CCA GTC CAA AGA Pro Ala Gln Arg Asp Gly Gly Ala Leu Gly Arg Gly Pro Trp Asp Ser
CCG GCT CAG CGT GAC GGT GGT GCT CTC GGG CGG GGC CCC TGG GAC TCC
GGC CGA GTC GCA CTG CCA CCA CGA GAG CCC GCC CCG GGG ACC CTG AGG Ser Asp Arg Ser Ala Leu Leu Lys Ser Lys Leu Arg Ala Leu Leu Thr
TCT GAT CGA TCT GCC CTC CTA AAA AGC AAG CTG AGG GCG CTG CTC ACT
AGA CTA GCT AGA CGG GAG GAT TTT TCG TTC GAC TCC CGC GAC GAG TGA
                                  Staph V8
                                     ↓
Ala Pro Arg Ser Leu Lys Phe Glu Arg Ser Ser Cys Phe Gly Gly Arg
GCC CCT CGG AGC CTG AAA TTC GAA CGC TCT TCT TGT TTC GGT GGT CGT
CGG GGA GCC TCG GAC TTT AAG CTT GCG AGA AGA ACA AAG CCA CCA GCA Met Asp Arg Ile Gly Ala Gln Ser Gly Leu Gly Cys Asn Ser Phe Arg
ATG GAT CGT ATC GGT GCT CAA TCT GGT TTG GGT TGT AAC TCT TTC AGA
TAC CTA GCA TAG CCA CGA GTT AGA CCA AAC CCA ACA TTG AGA AAG TCT Tyr STP Ala
TAC TAA GCT T
ATG ATT CGA A
```

FIG. 1

```
    Met Thr Met Ile Thr Asn Leu Thr Thr Thr Thr Thr Gln Phe Arg
CAT ATG ACC ATG ATT ACG AAT TTA ACC ACC ACC ACC ACC CAA TTC CGT
GTA TAC TGG TAC TAA TGC TTA AAT TGG TGG TGG TGG TGG GTT AAG GCA

Met Asn Pro Met Tyr Asn Ala Val Ser Asn Ala Asp Leu Met Asp Phe
ATG AAC CCG ATG TAC AAC GCA GTG TCC AAC GCA GAC CTG ATG GAT TTC
TAC TTG GGC TAC ATG TTG CGT CAC AGG TTG CGT CTG GAC TAC CTA AAG

Lys Asn Leu Leu Asp His Leu Gln Gln Lys Met Pro Leu Gln Asp Gln
AAG AAC CTG CTG GAC CAC CTG CAG CAG AAG ATG CCG CTG CAG GAT CAG
TTC TTG GAC GAC CTG GTG GAC GTC GTC TTC TAC GGC GAC GTC CTA GTC

Val Val Pro Pro Gln Val Leu Ser Gln Pro Asn Gln Gln Ala Gly Ala
GTT GTG CCG CCG CAG GTT CTG TCT CAA CCG AAC CAG CAG GCT GGT GCT
CAA CAC GGC GGC GTC CAA GAC AGA GTT GGC TTG GTC GTC CGA CCA CGA

Ala Leu Ser Pro Leu Pro Gln Val Pro Pro Trp Thr Gly Gln Val Ser
GCT CTG TCT CCG CTG CCG CAG GTT CCG CCG TGG ACC GGT CAG GTT TCT
CGA GAC AGA GGC GAC GGC GTC CAA GGC GGC ACC TGG CCA GTC CAA AGA

Pro Ala Gln Arg Asp Gly Gly Ala Leu Gly Arg Gly Pro Trp Asp Ser
CCG GCT CAG CGT GAC GGT GGT GCT CTC GGG CGG GGC CCC TGG GAC TCC
GGC CGA GTC GCA CTG CCA CCA CGA GAG CCC GCC CCG GGG ACC CTG AGG

Ser Asp Arg Ser Ala Leu Leu Lys Ser Lys Leu Arg Ala Leu Leu Thr
TCT GAT CGA TCT GCC CTC CTA AAA AGC AAG CTG AGG GCG CTG CTC ACT
AGA CTA GCT AGA CGG GAG GAT TTT TCG TTC GAC TCC CGC GAC GAG TGA

Staph V8
                               ↓
Ala Pro Arg Ser Leu Lys Phe Glu Arg Ser Ser Cys Phe Gly Gly Arg
GCC CCT CGG AGC CTG AAA TTC GAA CGC TCT TCT TGT TTC GGT GGT CGT
CGG GGA GCC TCG GAC TTT AAG CTT GCG AGA AGA ACA AAG CCA CCA GCA Met Asp Arg Ile Gly Ala Gln Ser Gly Leu Gly Cys Asn Ser Phe Arg
ATG GAT CGT ATC GGT GCT CAA TCT GGT TTG GGT TGT AAC TCT TTC AGA
TAC CTA GCA TAG CCA CGA GTT AGA CCA AAC CCA ACA TTG AGA AAG TCT Tyr STP Ala
TAC TAA GCT T
ATG ATT CGA A
```

FIG. 2

```
       Phe Glu Arg Ser Ser Cys Phe Gly Gly Arg Met Asp Arg Ile
EcoRI        1                           3
   AA TTC GAA CGC TCT TCT TGT TTC GGT GGT CGT ATG GAT CGT ATC
    G CTT GCG AGA AGA ACA AAG CCA CCA GCA TAC CTA GCA TAG
                    2                           4
```

```
Gly Ala Gln Ser Gly Leu Gly Cys Asn Ser Phe Arg Tyr STP
            5                           7        HindIII
 GGT GCT CAA TCT GGT TTG GGT TGT AAC TCT TTC ATA GAC -TAA AGC TTG
 CCA CGA GTT AGA CCA AAC CCA ACA TTG AGA AAG TAT CTG ATT TCG AAC
            6                           8
```

FIG. 3

```
            Met Thr Met Ile Thr Asn Leu Thr Thr Thr
   NdeI       1                    3
         ┌─────────────────────┬──────────────────────▶
         T ATG ACC ATG ATT ACG AAT TTA ACC ACC ACC
           AC TGG TAC TAA TGC TTA AAT TGG TGG TGG
         └─────────────────────┴──────────────────────▶
                     2
```

```
Thr Thr Glu Phe
        EcoRI       HindIII
─────────────────────────┐
ACC ACC GAA TTC ATT A
TGG TGG CTT AAG GCA TTC GA
─────────────────────────
            4
```

FIG. 4

```
        Leu Gly Arg Gly Pro Trp Asp Ser Ser Asp Arg Ser Ala Leu Leu Lys
        AvaI            1                           3
        ┌──────────────────────────────────────────────────────────────→
        TC  GGG CGG GGC CCC TGG GAC TCC TCT GAT CGA TCT GCC CTC CTA AAA
            C   GCC CCG GGG ACC CTG AGG AGA CTA GCT AGA CGG GAG GAT TTT
            └─────────────────────────────────────────────────────────→
                        2                           4

Ser Lys Leu Arg Ala Leu Leu Thr Ala Pro Arg Ser Leu Lys Phe
                    5                           7               EcoRI
        ┌─────────────────────────────────────────────────────────┐
        AGC AAG CTG AGG GCG CTG CTC ACT GCC CCT CGG AGC CTG A
        TCG TTC GAC TCC CGC GAC GAG TGA CGG GGA GCC TCG GAC TTT AA
        └─────────────────────────────────────────────────────────
                    6                           8
```

FIG. 5

```
 Glu Phe Arg Met Asn Pro Met Tyr Asn Ala Val Ser Asn Ala Asp Leu
 EcoRI        1                               3
┌─────────────────────────────────────────────────┐
│ AA TTC CGT ATG AAC CCG ATG TAC AAC GCA GTG TCC AAC GCA GAC CTG
│    G GCA TAC TTG GGC TAC ATG TTG CGT CAC AGG TTG CGT CTG GAC ──→
└─────────────────────────────────────────────────┘
                       2
```

```
 Met Asp Phe Lys Asn Leu Leu Asp His Leu Gln Gln Lys Met Pro Leu
                          5
─────────────────────────────────────────────────────────────────→
 ATG GAT TTC AAG AAC CTG CTG GAC CAC CTG CAG CAG AAG ATG CCG CTG
 TAC CTA AAG TTC TTG GAC GAC CTG GTG GAC GTC GTC TTC TAC GGC GAC
─────────────────────────────────────────────────────────────────
           4                                         6
```

```
 Gln Asp Gln Val Val Pro Pro Gln Val Leu Ser Gln Pro Asn Gln Gln
          7                                    9
─────────────────────────────────────────────────────────────────→
 CAG GAT CAG GTT GTG CCG CCG CAG GTT CTG TCT CAA CCG AAC CAG CAG
 GTC CTA GTC CAA CAC GGC GGC GTC CAA GAC AGA GTT GGC TTG GTC GTC
─────────────────────────────────────────────────────────────────
                       8                              10
```

```
 Ala Gly Ala Ala Leu Ser Pro Leu Pro Gln Val Pro Pro Trp Thr Gly
                  11                              13
─────────────────────────────────────────────────────────────────→
 GCT GGT GCT GCT CTG TCT CCG CTG CCG CAG GTT CCG CCG TGG ACC GGT
 CGA CCA CGA CGA GAC AGA GGC GAC GGC GTC CAA GGC GGC ACC TGG CCA
─────────────────────────────────────────────────────────────────
                          12
```

```
 Gln Val Ser Pro Ala Gln Arg Asp Gly Gly Ala Leu
                      15                    AvaI
─────────────────────────────────────────────────┐
 CAG GTT TCT CCG GCT CAG CGT GAC GGT GGT GCT C   │
 GTC CAA AGA GGC CGA GTC GCA CTG CCA CCA CGA GCC │
─────────────────────────────────────────────────┘
           14                      16
```

FIG. 6

EXPRESSION OF RECOMBINANT POLYPEPTIDES WITH IMPROVED PURIFICATION

DESCRIPTION

1. Technical Field

This invention relates to the molecular biology of hormonal peptide factors and recombinant DNA technology. More specifically, this invention relates to atrial natriuretic peptide (ANP), its therapeutic use, and processes for producing active ANP.

2. Background of the Invention

Although the production of proteins and peptides by recombinant expression has become relatively common, the expression and subsequent purification of proteins and peptides in an active form having sufficient purity for pharmaceutical administration or diagnostic assay is still a difficult and complicated task. When one is further constrained to use of only commercially feasible processes, the task is perplexing.

Recombinant expression of peptides is typically accomplished by inserting a DNA sequence encoding the desired peptide into an expression vector. The expression vector generally contains regulatory sequences which are recognized by the host cell, which provide for transcription and translation of the inserted DNA into the peptide. The expression vector is then inserted into a suitable host cell, typically a bacterium, yeast, or mammalian cell in culture. The expression vector also usually includes a selectable marker, so that one may identify those cells which have been successfully transformed and carry the vector, and separate them from those which do not carry the vector.

Peptides may be expressed either "directly" or in the form of a fusion protein. Direct expression produces the desired peptide without modification, but often results in low yields with small peptides. Most host cells appear able to recognize heterologous peptides and effect their degradation.

Fusion proteins comprise a leader protein of significant size which is joined to the peptide of interest. The leader protein is often native to the host, as in the case of β-galactosidase. The fusion protein results from expression of a vector containing the coding sequence for the leader protein coupled to the coding sequence for the peptide, joined in the same reading frame. Fusion proteins are often used with small peptides, as the use of the larger endogenous leader protein tends to minimize degradation of the heterologous peptide. However, purification of the fusion protein is often difficult as it often forms insoluble inclusion bodies in the host cell. Use of an endogenous leader protein also hampers separation of the fusion protein from other proteins endogenous to the cell. Further, in order to obtain an authentic peptide one must cleave the leader protein and separate it from the desired peptide. Thus, significantly more processing is required, which leads to loss of product.

F. J. Bailey et al, J Indust Microbiol (1987) 2:47-52 disclosed expression of atrial natriuretic peptide (ANP) in E. coli as a fusion protein using CheY as the leader protein.

Brewer et al, U.S. Pat. No. 4,880,911, disclosed expression of urogastrone (epidermal growth factor) as a fusion protein with a highly-charged amino acid polymer. The peptide is expressed with a C-terminal extension of basic amino acids, preferably 2-30 Arg residues. Following expression, the fusion protein may be isolated using the high positive charge imparted by the poly-Arg tail. The tail may be removed using an exopeptidase such as carboxypeptidase C.

W. L. Sung et al, Proc Nat Acad Sci USA (1986) 83:561-65 disclosed expression of proinsulin as fusion proteins having a short (eight amino acid) β-galactosidase leader followed by six or seven repeats of each amino acid, fused to the amino terminus of proinsulin by a linker cleavable with CNBr. Sung found that fusion proteins wherein the hexamer or heptamer was Gln, Asn, Thr, Ser, Ala, His, or Cys (e.g., β-gal-Gln$_6$-proinsulin) were expressed to the greatest degree.

Shen et al, EP 163,406, disclosed a method for expressing small peptides as fusion proteins containing a leader protein and multiple copies of the peptide in tandem repeats. Shen used β-galactosidase as the leader protein, and separated multiple copies of insulin with cleavable linker sequences (cleaving with trypsin and carboxypeptidase B). See also S. Cockle et al, "Protein Purification: Micro to Macro" (1987, Alan R. Liss, Inc) pp. 375-81.

Cohen et al, U.S. Pat. No. 4,743,679 disclosed the expression of epidermal growth factor (EGF) as a fusion protein with a leader of up to 200 amino acids (preferably up to 75). The leader and EGF peptides are joined by a Glu residue, providing for cleavage by Staph V8. The tertiary structure of EGF apparently protected its internal Glu residues from cleavage by V8. The fusion protein was expressed in bacteria as an insoluble inclusion body. The leader polypeptide was selected to have only one Met (at the N-terminal) and one Glu (where it was joined to EGF) and to exclude Cys.

Hobden et al, GB 2,180,539, disclosed a method for producing ANP by expressing the peptide as a fusion protein with a carrier polypeptide. The carrier polypeptide reduced degradation of the short ANP peptide. The fusion protein consisted of a carrier polypeptide joined to the ANP peptide through a linker containing a site cleaved by a protease. The proteases disclosed were mammalian gut proteolytic enzyme enterokinase, thrombin, plasmin, collagenase, Staph V8, Factor Xa and endopeptidase lys C. The preferred carrier polypeptide was derived from the E. coli chloramphenicol acetyltransferase (CAT) gene. Hobden suggested that the fusion protein may be purified prior to proteolysis, and may be assayed based on the immunological characteristics of the carrier polypeptide.

Mai et al, EP 207,044 disclosed the expression of small peptides as fusion proteins comprising an endogenous polypeptide leader, an endopeptidase "trigger signal" (cleavage site), and the peptide. Mai taught that it is preferred to avoid trigger signals in the leader protein so that a clean release of the peptide can be achieved. The maintenance of the integrity of the endogenous protein also simplifies subsequent purification of the peptide.

The proteases disclosed in Mai were trypsin, plasmin, enterokinase, kallikrein, urokinase, tPA, clostripain, chymotrypsin, pepsin, chymosin, collagenase, Russell's viper venom protease, post-proline cleaving enzyme, Staph V8, factor Xa, and thrombin, with Staph V8, factor Xa, and thrombin being preferred. The endogenous proteins suitable for use as leaders disclosed were chloramphenicol acetyltransferase (CAT), β-galactosidase, and recA.

RecA is a nuclear protein found in E. coli and other organisms which interacts with DNA, and has a high negative charge. Mai disclosed that using recA as the leader protein improves purification of the subsequent fusion protein, as one can employ techniques such as anion exchange chromatography to isolate recA proteins from other bacterial proteins. Mai separated recA fusion proteins from other bacterial proteins by applying the cell paste extract to an anion exchange column and eluting with either an NaCl gradient or an NH$_4$Cl gradient, which removed ~80% of the bacterial proteins. After the fusion protein was cleaved with V8 protease, the heterologous protein was separated from the recA portion either by binding to an anion exchange resin or by reversed phase HPLC.

Atrial natriuretic peptide (ANP) is a 3 kDa peptide found in atrial muscle cells which exhibits potent diuretic and natriuretic activities, as well as vasorelaxation. It is normally expressed in the form of a propeptide, having a long pro segment (14-16 kDa) at the amino terminus. ANP is disclosed in Johnson et al, U.S. Pat. No. 4,764,504, filed May 8, 1985, and USSN 870,795, filed Jun. 5, 1986, both incorporated herein by reference.

DISCLOSURE OF THE INVENTION

We have now developed an improved method for expressing peptides as fusion proteins, by using the pro portion of human proANP as the carrier for a heterologous peptide, wherein each of the Glu residues normally present in the pro-ANP pro portion is altered to Gln, for example, by site-directed mutagenesis. The proANP pro portion and heterologous peptide are joined by a V8 cleavage site, which permits cleavage using *Staphylococcus aureas* V8 protease. Alternatively, other proteases and chemical cleavage methods can be used to obtain the final peptide of the invention, using the peptide expression methods described herein. The altered proANP pro portion exhibits a high isoelectric point, which facilitates separation of the fusion protein from all other host cell proteins, nucleic acids, pyrogens, and the like, and separation of the carrier from the peptide after cleavage.

BRIEF DESCRIPTION OF THE DRAWINGS

FIG. 1 provides the nucleotide sequence and amino acid sequence for the vector phNF117. The β-gal-(thr)6 leader peptide amino acid sequence is listed in italics, while the pro-ANP sequence is shown in normal type. The ANP portion of the amino acid sequence is shown in bold type. Residues which have been altered from Glu to Gln are underlined.

FIG. 2 lists the nucleotide sequence and amino acid sequence for the vector phNF120-1. The β-gal-(thr)6 leader peptide amino acid sequence is listed in italics, while the pro-ANP sequence is shown in normal type. The ANP portion of the amino acid sequence is shown in bold type. Residues which have been altered from Glu to Gln are underlined.

FIG. 3 shows the synthetic oligonucleotides used to prepare an ANP coding sequence having a Staph V8 cleavage site.

FIG. 4 shows the synthetic oligonucleotides used to prepare a β-gal-(thr)6 leader peptide coding sequence having a Staph V8 cleavage site used in phNF117, as described in Example 1(b).

FIG. 5 shows the synthetic oligonucleotides used to prepare a synthetic proANP peptide coding sequence having a Staph V8 cleavage site used in phNF117, as described in Example 1(c).

FIG. 6 shows the synthetic oligonucleotides used to prepare a synthetic proANP peptide coding sequence having a Staph V8 cleavage site used in phNF117, as described in Example 1(d).

FIG. 7(A) shows the chromatogram obtained from an ANP fusion protein of the invention purified on carboxymethyl-Sepharose ®. FIG. 7(B) shows the chromatogram obtained from an ANP fusion protein of the invention obtained by RP-HPLC pre- and post-cleavage with Staph-V8 protease. FIG. 7(C) shows the chromatogram of purified ANP obtained from an ANP fusion protein of the invention.

MODES OF CARRYING OUT THE INVENTION

A. Definitions

Figure 7A:
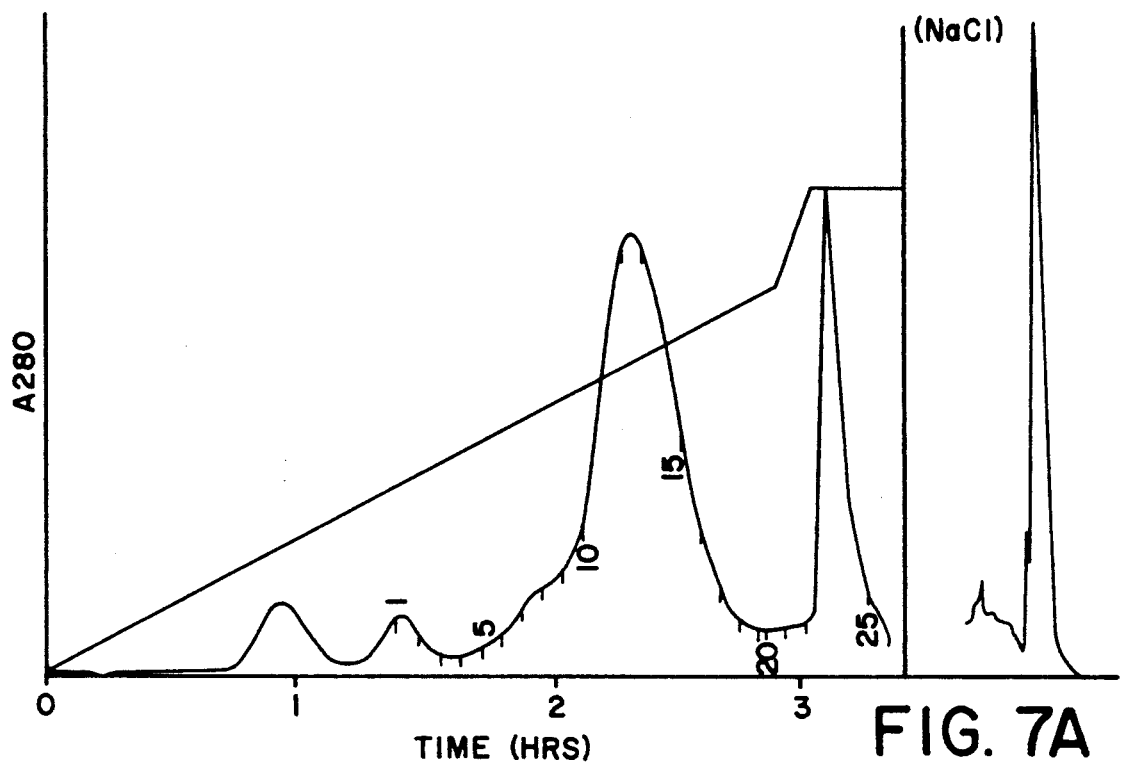
FIGS. 7A to G depict three chromatograms obtained by RP-HPLC.

The term "fusion protein" as used herein refers to a chimeric polypeptide having a general form:

(leader)-carrier-cleavage site-heterologous peptide, wherein "heterologous peptide" denotes a polypeptide of up to about 10 kDa which exhibits biological activity, antigenic activity, or the like; "cleavage site" indicates an amino acid sequence which is hydrolyzed by *Staphylococcus aureas* V8 protease or other selected specific protease or proteolytic method; "carrier" denotes a polypeptide of about 10 to about 50 kDa; and "leader" denotes an optional leader sequence. In some cases the leader sequence may be used for directing secretion of the fusion protein.

The term "heterologous peptide" as used herein will generally refer to a peptide which is not endogenous to the host selected, although this definition will also include endogenous peptides in cases in which overexpression of such is desired. Heterologous peptides are short relative to most proteins, generally having a molecular weight of less than about 10 kDa, and may be glycosylated, sialylated, phosphorylated, or the like. The peptide will also exhibit some form of useful activity, typically either biological activity (for example as a peptide hormone), or antigenic activity, for use in recombinant vaccines and/or immunological assays. The peptide will not include an accessible V8 cleavage site, so that the peptide is not fragmented during separation from the carrier protein. The peptide may either omit any cleavage site, or may express a site in an inaccessible portion of the peptide (e.g., at a position of the peptide which is masked by another portion of the peptide, or by gly-cosylation, phosphorylation, or the like). Peptide which naturally include a cleavage site for the selected protease may be altered, e.g., by site-specific mutagenesis, to a form in which the site is no longer present in cases where the activity of the peptide may be preserved. Representative peptides within the scope of the invention include, without limitation, atrial natriuretic peptide (ANP), brain natriuretic peptide, somatostatin, glucagon-like peptide, calcitonin, lung surfactant, insulin, growth hormone releasing factor (GRF), bradykinins, endorphins, enkephalins, and the like.

The term "carrier protein" refers to a protein which stabilizes expression of a heterologous peptide, and, together with a heterologous peptide forms the fusion protein of the invention. The carrier protein will generally have a molecular weight of about 10 to about 50 kDa, and preferably will not have an accessible internal cleavage site. The carrier protein also serves to raise the pI of the resulting fusion protein to a range that permits facile separation of the fusion protein from endogenous host cell proteins. A pI of about 8.0 or greater is presently preferred. The carrier protein may be derived from an endogenous host protein or fragment thereof, or may consist of a random sequence of high basicity. Preferably, the carrier protein will not contain Glu or Asp-Gly residues, to avoid cleavage by V8 into a large number of fragments. A presently preferred carrier protein is derived from the pro region of human proANP by altering each Glu residue to a neutral or basic amino acid. The preferred carrier protein has essentially the following sequence:

Asn—Pro—Met—Tyr—Asn—Ala—Val—Ser—Asn—Ala—Asp—
Leu—Met—Asp—Phe—Lys—Asn—Leu—Leu—Asp—His—Leu—
$X_1$—$X_2$—Lys—Met—Pro—Leu—$X_3$—Asp—$X_4$—Val—Val—Pro—
Pro—Gln—Val—Leu—Ser—$X_5$—Pro—Asn—$X_6$—$X_7$—Ala—
Gly—Ala—Ala—Leu—Ser—Pro—Leu—Pro—$X_8$—Val—Pro—
Pro—Trp—Thr—Gly—$X_9$—Val—Ser—Pro—Ala—Gln—Arg—
$X_{10}$—$X_{11}$—Gly—Ala—Leu—Gly—Arg—Gly—Pro—Trp—Asp—
Ser—Ser—Asp—Arg—Ser—Ala—Leu—Leu—Lys—Ser—Lys—
Leu—Arg—Ala—Leu—Leu—Thr—Ala—Pro—Arg—Ser—
Leu—Lys—Phe—;

where $X_{1-9}$ are neutral or basic amino acids, and $X_{10}$ and $X_{11}$ are amino acids other than Glu, selected to avoid the dipeptide sequence Asp-Gly (i.e., $X_{11}$ is not Asp, and if $X_{10}$ is Asp then $X_{11}$ is not Gly or Asp). In the presently-preferred embodiment, $X_{1-9}$ are each Gln.

B. General Method

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored and religated in the form desired.

Site specific DNA cleavage is performed by treatment with a suitable restriction enzyme (or enzymes) under conditions which are generally understood in the art, generally following the manufacture's directions. See, e.g., T. Maniatis et al, "Molecular Cloning: A Laboratory Manual" (New York, Cold Spring Harbor Laboratory, 1982). In general, about 1 μg of plasmid or DNA sequence is cleaved by one unit enzyme in about 20 μL of buffer solution; in the examples herein, typically, an excess of restriction enzyme is used to insure complete digestion of the DNA substrate. Incubation times of about 1 hr to 2 hr at about 37° C. are workable, although variations can be tolerated. After each incubation, protein is removed by extraction with phenol/-chloroform, and may be followed by diethyl ether extraction, and the nucleic acid recovered from aqueous fractions by ethanol precipitation followed by separation over a Sephadex ® G-50 spin column. If desired, size separation of the cleaved fragments may be performed by polyacrylamide gel or agarose gel electrophoresis using standard techniques. A general description of size separations is found in Meth Enzymol (1980) 65:499–560.

Restriction cleaved fragments may be blunt ended by treating with the large fragment of E. coli DNA polymerase I (Klenow) in the presence of the four deoxyribonucleotide triphosphates (dNTPs) using incubation times of about 15 to 25 min at 20° to 25° C. in 50 mM Tris, pH 7.6, 50 mM NaCl, 6 mM MgCl$_2$, 6 mM DTT and 5–10 μM dNTPs. The Klenow fragment fills in at 5' sticky ends but chews back protruding 3' single strands, even though the four dNTPs are present. If desired, selective repair can be performed by supplying only 1–3 of the dNTPs, within the limitations dictated by the nature of the sticky ends. After treatment with Klenow fragment, the mixture is extracted with phenol/-chloroform and ethanol precipitated followed by running over a Sephadex ® G-50 spin column. Treatment under appropriate conditions with S1 nuclease results in hydrolysis of any single-stranded portion.

Synthetic oligonucleotides are prepared by the triester method of Matteucci et al (J Am Chem Soc (1981) 103:3185) or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM MgCl$_2$, 5 mM dithiothreitol, 1–2 mM ATP, 1.7 pmoles $^{32}$P-ATP (2.9 mCi/mmole), 0.1 mM spermidine, and 0.1 mM EDTA.

Ligations are performed in 15–30 μL volumes under the following standard conditions and temperatures: 20 mM Tris-HCl, pH 7.5, 10 mM MgCl$_2$, 10 mM DTT, 33 μg/mL BSA, 10 mM-50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/mL total DNA concentrations (5–100 nM total end concentration). Intermolecular blunt end ligations (usually employing a 10–30 fold molar excess of linkers) are performed at 1 μM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{2+}$ using about 1 unit of BAP per μg of vector at 60° C. for about 1 hr. In order to recover the nucleic acid fragments, the preparation is extracted with phenol/-chloroform and ethanol precipitated and desalted by application to a Sephadex ® G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis may be used. This is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having the mutated form as a single strand; 50% will have the original sequence. The resulting plaques are hybridized with kinased synthetic primer under allele-specific conditions. In general, one may vary the temperature, ionic strength, and concentration of chaotropic agent(s) in the hybridization solution to obtain conditions under which substantially no probes will hybridize in the absence of an "exact match." For hybridization of probes to bound DNA, the empirical formula for calculating optimum temperature under standard conditions (0.9M NaCl) is $$T(°C.)=4(N_G+N_C)+2(N_A+N_T)-5° C.,$$

where $N_G$, $N_C$, $N_A$, and $N_T$ are the numbers of G, C, A, and T bases in the probe (J. Meinkoth et al, *Anal Biochem* (1984) 138:267–84).

Plaques which hybridize with the probe are then picked, cultured, and the DNA recovered.

Verification of Construction

Correct ligations for plasmid construction may be confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the plasmid construction, as is understood in the art. Plasmids from the transformants are then prepared according to the method of D. B. Clewell et al, *Proc Nat Acad Sci USA* (1969) 62:1159, optionally following chloramphenicol amplification (D. B. Clewell, *J Bacteriol* (1972) 110:667). The isolated DNA is analyzed by restriction and/or sequenced by the dideoxy method of F. Sanger et al, *Proc Nat Acad Sci USA* (1977) 74:5463 as further described by Messing et al, *Nucleic Acids Res* (1981) 9:309, or by the method of Maxam et al, *Methods in Enzymol* (1980) 65:499.

Expression

The proteins of the invention may be expressed in either prokaryotic or eukaryotic systems. Prokaryotes are most frequently represented by various strains of *E. coli*. However, other microbial strains may also be used, such as bacilli (for example *Bacillus subtilis*), various species of Pseudomonas, and other bacterial strains. In such prokaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al, *Gene* (1977) 2:95. Commonly used prokaryotic control sequences, which are defined herein to include promoters for transcription initiation, along with ribosome binding site sequence, include such commonly used promoters as the β-lactamase (penicillinase) and lactose (lac) promoter systems (Chang et al, *Nature* (1977) 198:1056), the tryptophan (trp) promoter system (Goeddel et al, *Nuc Acids Res* (1980) 8:4057), and the lambda-derived $P_L$ promoter and N-gene ribosome binding site (Shimatake et al, *Nature* (1981) 292:128). However, any available promoter system compatible with prokaryotes can be used.

The expression systems useful in eukaryotic systems of the invention comprise promoters derived from appropriate eukaryotic genes. A class of promoters useful in yeast, for example, include promoters for synthesis of glycoltic enzymes, including those for 3-phosphoglycerate kinase (Hitzeman et al, *J Biol Chem* (1980) 255:2073). Other promoters include those from the enolase gene (M. J. Holland et al, *J Biol Chem* (1981) 256:1385) or the Leu2 gene obtained from YEp13 (J. Broach et al, *Gene* (1978) 8:121).

Suitable mammalian promoters include the early and late promoters from SV40 (Fiers et al, *Nature* (1978) 273:113) or other viral promoters such as those derived from polyoma, adenovirus II, bovine papilloma virus, or avian sarcoma viruses. Suitable viral and mammalian enhancers are cited above. In the event plant cells are used as an expression system, the nopaline synthesis promoter is appropriate (A. Depicker et al, *J Mol Appl Gen* (1982) 1:561). Expression insect cell culture may conceniently be achieved using a baculovirus vector, for example, transfer vectors derived from the baculovirus *Autographa californica* nuclear polyhedrosis virus (AcNPV), (see PCT WO89/046699).

Transformation

Depending on the host cell used, transformation is accomplished using standard techniques appropriate to such cells. The calcium treatment employing calcium chloride, as described by S. N. Cohen, *Proc Nat Acad Sci USA* (1972) 69:2110, or the RbCl method described in Maniatis et al, supra, p. 254, is used for prokaryotes or other cells which contain substantial cell wall barriers. Infection with *Agrobacterium tumefaciens* (C. H. Shaw et al, *Gene* (1983) 23:315) is used for certain plant cells. For mammalian cells without cell walls, the calcium phosphate precipitation method of Graham and van der Eb, *Virology* (1978) 52:546 is preferred. Transformations into yeast are carried out according to the method of P. Van Solingen et al, *J Bacter* (1977) 130:946 and C. L. Hsiao et al, *Proc Nat Acad Sci USA* (1979) 76:3829.

C. Examples

The examples presented below are provided as a further guide to the practitioner of ordinary skill in the art, and are not to be construed as limiting the invention in any way.

EXAMPLE 1

Construction of plasmid phNF75

A plasmid was constructed which fuses human atrial natriuretic peptide (hANP4-28), to *E. coli* β-galactosidase (amino acid 1005 at the EcoRI site) with an Endoproteinase Glu-C (Staph V8) cleavage site (Boehringer Mannheim) at their junction. The hybrid gene is transcribed from the lacZ promoter/operator region on a pBR322-based plasmid.

First, a synthetic DNA fragment encoding the cleavage site, hANP(4-28), and translation termination signal was assembled from eight oligodeoxyribonucleotides (FIG. 3) by the method of G. P. Vlasuk et al, *J Biol Chem* (1986) 261:4789-96, and purified from a 8% polyacrylamide gel (T. Maniatis et al, supra, p. 173–178). Some *E. coli* preferred codon choices (M. Gouy et al, *Nuc Acids Res* (1982) 10:7055-74) were utilized in the design of the synthetic gene which was designated hANP* (the asterisk denoting the presence of the proteolytic cleavage site). About 200 ng of this fragment was mixed with 20 ng of M13mp19 (C. Yanisch-Perron et al, *Gene* (1985) 33:103-19) which had been digested with restriction endonucleases EcoRI and SmaI (New England Biolabs, using conditions recommended by manufacturer) to linearize the vector; 400 U of T4 DNA ligase (New England Biolabs) and ligase buffer (final concentration 50 mM Tris-HCl, pH 7.4, 10 mM MgCl$_2$, 10 mM DTT, 0.3 mM ATP) were added and the DNAs incubated overnight at 15° C. *E. coli* JM101 (0.1 mL) made competent by the CaCl$_2$ procedure (Maniatis et al, supra, p. 250–51) was transfected with the ligation, mixed with 0.2 mL of JM101 overnight culture, added to L-top agarose with 5-bromo-4-chloro-3-indolyl-β-D-galactoside, i.e., X-gal (50 μL of 2% solution in dimethylformamide) and isopropyl-β-D-thiogalactopyranoside (IPTG) (10 μL of 100 mM solution in water) and poured on the surface of an L-plate. After overnight incubation at 37° C., a white plaque was chosen (M13-hNF7), a phage stock grown, and single-stranded DNA prepared (J. Messing, *Meth Enzymol* (1983) 101:20–78) for sequencing by the method of F. Sanger et al, *Proc Nat Acad Sci USA* (1977) 74:5463–67. The DNA sequence of the synthetic hANP* fragment was shown to be correct.

Second, double-stranded DNA from M13-hNF7 (Messing, supra) was prepared and digested with restriction endonucleases BamHI and BglII (New England Biolabs) and the approximately 700 bp DNA fragment containing the hANP* sequence was purified from a 0.6% agarose gel (Maniatis et al, supra, pp. 157–161). Plasmid pTrp-233 (prepared as described in U.S. Pat. No. 4,764,504) was digested with restriction endonuclease BamHI, its termini dephosphorylated by incubation with bacterial alkaline phosphatase (Amersham) by the method of Maniatis et al (supra, p. 133), and the linearized plasmid purified from a 0.6% agarose gel. Approximately 100 ng of the BamHI-BglII DNA fragment was mixed with 20 ng of the linearized plasmid and 400 U of T4 DNA ligase and ligation buffer added for overnight incubation at 15° C. Competent *E. coli* MC1061 was transformed with the ligation and incubated overnight on L-plates with 100 μg/mL ampicillin at 37° C. Colonies were inoculated into L-broth containing 100 μg/mL ampicillin, grown overnight, and 1 mL withdrawn to prepare plasmid DNA by the alkaline lysis method of Maniatis et al, (supra, p. 368–369). The orientation of the BamHI-BglII fragment within the plasmid was determined by digestion with restriction endonucleases PvuII and HindIII (New England Biolabs) and sizing of the DNA fragments on a 0.6% agarose gel. The desired orientation placed the BamHI recognition site of the fragment next to the EcoRI recognition site of the plasmid creating an hANP* cassette which could be released as an EcoRI-HindIII, EcoRI-BamHI, or EcoRI-EcoRI fragment. A plasmid with this orientation was designated phNF73.

Next, phNF73 was digested with restriction endonuclease EcoRI and the approximately 100 bp EcoRI-EcoRI fragment encoding hANP* was purified from an 8% polyacrylamide gel. Next 2 μg of plasmid pBgal was digested with restriction endonuclease EcoRI, the linearized plasmid purified from a 0.6% agarose gel, and its termini dephosphorylated by incubation with bacterial alkaline phosphatase. Then about 20 ng of linearized plasmid was mixed with about 50 ng of the EcoRI-EcoRI fragment and 400 U of T4 DNA ligase and ligation buffer added for overnight incubation at 15° C. Competent *E. coli* MC1061 were transformed with the ligation and incubated overnight at 37° C. on L-plates with 100 μg/mL ampicillin. One plasmid shown to contain the EcoRI-EcoRI fragment by digestion with EcoRI was designated phNF75. In several *E. coli* strains, phNF75 was shown to produce a hybrid protein of the expected size for a fusion of β-galactosidase and hANP(4-28) using SDS polyacrylamide gel electrophoresis (U. Laemmli, *Nature* (1970) 277:680–85). The fusion protein was partially purified, digested with Endoproteinase Glu-C (Staph V8), purified, and shown to have the correct amino acid sequence (data not shown).

(b) Construction of pTRP83-1

Plasmid pTRP83-1, which expresses a short β-gal leader peptide from the tryptophan promoter was constructed as follows:

Plasmid pTrp-233 (prepared as described in U.S. Pat. No. 4,764,504) was used to construct an expression vector encoding five amino-terminal residues of *E. coli* β-galactosidase followed by the sequence -Asn-Leu-Thr-Thr-Thr-Thr-Thr-Thr-Glu-Phe-(i.e., β-gal-(thr)6 leader peptide) under the control of the *E. coli* tryptophan promoter/operator region on a pBR322-based plasmid. FIG. 4 illustrates preparation of this sequence from four synthetic oligonucleotides. If desired, one may substitute the sequence -Asn-Leu-Thr-Thr-Thr-Thr-Thr-Thr-Gln-Phe- for the above by altering the appropriate oligonucleotides shown in FIG. 4. EcoRI and HindIII recognition sites downstream of this sequence permit fusion of genes, in frame, with the short leader peptide. This and other related peptides have been shown to stabilize the expression of proinsulin in *E. coli* (W. L. Sung et al, *Proc Nat Acad Sci USA* (1986) 83:561–65).

First, 2 μg of pTrp-233 were digested with EcoRI and the linearized plasmid purified from a 0.6% agarose gel. The termini were then filled in by the method of Maniatis et al (supra, p. 394), using the Klenow fragment of *E. coli* DNA polymerase I (Boehringer-Mannheim, Inc.). The mixture was then heated to 70° C. for 5 min to inactivate the enzyme and T4 DNA ligase was added with ligation buffer for overnight incubation at 15° C. *E. coli* MC1061 were made competent by the CaCl₂ method and transformed as described by Maniatis et al (supra, pp. 250–251). Resulting ampicillin-resistant colonies were grown overnight in L-broth with 100 μg/mL ampicillin and 1 mL aliquots withdrawn to prepare plasmid DNA by the alkaline lysis method of Maniatis et al (supra, pp. 368–369). A plasmid which had lost the EcoRI recognition site, as determined by failure to be digested by EcoRI, was designated pTRP81-6.

Next, 2 μg of plasmid pTRP81-6 was digested with HindIII and NdeI and linearized plasmid purified from a 0.6% agarose gel. A synthetic NdeI-HindIII DNA fragment encoding the β-gal-(thr)6 leader peptide was assembled from four oligodeoxyribonucleotides (FIG. 4) using the method of Vlasuk et al (supra) and purified from a 20% polyacrylamide gel (Maniatis et al, supra). This fragment encodes EcoRI and HindIII recognition sites for the fusion of genes, in frame, with β-galactosidase and the termini are nonphosphorylated. A thousandfold excess of the synthetic fragment was added to the linearized plasmid, mixed with T4 DNA ligase and ligation buffer, and incubated overnight at 15° C.; the ligation was used to transform competent *E. coli* MC1061 to ampicillin resistance. Colonies were grown, plasmid DNA prepared, and an EcoRI digest used to identify a plasmid containing the synthetic fragment, designated pTRP83-1. The correct sequence of the synthetic DNA fragment encoding the leader peptide was confirmed by the method of Sanger et al (supra).

(c) Construction of phNF86

Plasmid phNF86, which expresses a β-gal-(thr)6-proANP* hybrid protein from the tryptophan promoter, was constructed as follows:

Plasmids phNF-233 (prepared as in U.S. Pat. No. 4,764,504), phNF75 (see section a above), and pTRP83-

1 (see section b above) were used to construct an expression vector encoding the β-gal-(thr)6 leader peptide followed by proANP8 which contains an Endoproteinase Glu-C (Staph V8) cleavage site between pro and hANP(4-28) sequences. The hybrid protein is under the control of the *E. coli* tryptophan promoter/operator region on a pBR322-based plasmid.

First, plasmid phNF-233 was partially digested with AvaI and completely digested with HindIII to linearize the plasmid and remove the 3'-end of the proANP gene (from AvaI to HindIII). The linearized plasmid was purified from a 0.6% agarose gel. Plasmid phNF75 was digested with EcoRI and HindIII and the fragment encoding the hANP(4-28) gene with Endoproteinase Glu-C (Staph V8) cleavage site was purified from a 20% polyacrylamide gel. A synthetic DNA fragment encoding proANP sequences from the AvaI recognition site to the EcoRI site of the hANP* fragment (FIG. 5) was assembled from eight oligodeoxyribonucleotides by the method of Vlasuk et al (supra) and purified from an 8% polyacrylamide gel. The DNA sequence had been modified on this fragment so that ligation of the single-stranded tail with the complementary EcoRI tail destroys the EcoRI site (GAATTC changed to AAATTC); the termini are also nonphosphorylated. The three DNAs were mixed (about 50 ng of plasmid backbone, 100 ng of synthetic fragment, and at least 100 ng of hANP* fragment) with T4 DNA ligase and ligation buffer, and incubated overnight at 15° C. The ligation used to transform competent *E. coli* MC1061, ampicillin-resistant colonies grown in culture and plasmid DNA prepared for restriction endonuclease digestion with EcoRI and HindIII to confirm the insertion of the two DNA fragments into the plasmid. The correct DNA sequence was confirmed for the new proANP* using the method of Sanger et al (supra) in a plasmid designated phNF82.

Next, plasmid phNF82 was digested with NdeI and the termini filled in with the Klenow fragment of *E. coli* DNA polymerase I; the blunted linearized plasmid was mixed with a nonphosphorylated EcoRI linker (5'-CGGAATTCCG-3', New England Biolabs) and T4 DNA ligase for overnight incubation at 15° C. The ligation was then extracted with phenol:chloroform, ethanol precipitated, and digested with EcoRI and HindIII to release the proANP gene as an EcoRI-HindIII fragment purified from a 0.6% agarose gel. Plasmid pTRP83-1 was digested with EcoRI and HindIII to linearize the plasmid and purified from a 0.6% agarose gel. The DNA fragment and the linearized plasmid were mixed with the T4 DNA ligase and ligation buffer and incubated overnight at 15° C. Competent *E. coli* MC1061 were transformed with the ligation and ampicillin-resistant colonies grown as overnight cultures for plasmid DNA. Digestion of plasmid DNA with EcoRI and HindIII identified a plasmid containing the proANP gene, designated phNF86. Upon the addition of 3-β-indoleacrylic acid (25 μg/mL) to induce the tryptophan promoter, several strains of *E. coli* carrying plasmid phNF86 expressed the hybrid protein at 10-15% of total cell protein in shake flask cultures (data not shown). The expression level was estimated by densitometer scan of Coomassie blue-stained SDS polyacrylamide gels.

(d) Construction of plasmid phNF117

Plasmid phNF117, which expresses a β-gal-(thr)6-proANP* gln hybrid protein from the tryptophan promoter, was constructed as follows:

Plasmid phNF86 was modified to reduce the number of endoproteinase Glu-C (Staph V8) cleavage sites (Boehringer Mannheim) within the proANP region. Only two sites remain in the modified plasmid: the first at the junction between the β-gal-(thr)6 leader peptide and the proANP region and the second between the proANP region and the hANP(4-28) peptide (FIG. 1). This was accomplished by changing nine glutamic acid residues to glutamine residues; preferred *E. coli* codon choice (Gouy et al, supra) was also introduced in the region which was modified.

First, plasmid phNF86 was digested with EcoRI and HindIII and the fragment encoding proANP* purified from a 0.6% agarose gel. Plasmid pUC8 (J. Vieira et al, *Gene* (1982) 19:252) was digested with EcoRI and HindIII and the linearized plasmid purified from a 0.6% agarose gel. DNA fragment (500 ng) and linearized plasmid (100 ng) were mixed, incubated with T4 DNA ligase and ligation buffer overnight at 15° C. and the ligation used to transform competent *E. coli* MC1061 to ampicillin resistance. A plasmid containing the proANP* fragment was designated pUC-hNF114.

Next, the EcoRI-AvaI DNA sequence of the proANP fragment was removed by digestion with EcoRI and AvaI and purification of the plasmid on a 0.6% polyacrylamide gel. A synthetic DNA fragment to replace this region was assembled from sixteen oligodeoxyribonucleotides using the method of Vlasuk et al (supra) (FIG. 6). The sequence of the fragment incorporates both preferred *E. coli* codons and the replacement of nine glutamic acid residues by glutamine residues. The nonphosphorylated synthetic DNA fragment was purified from an 8% polyacrylamide gel and at least 200 ng mixed with 50 ng of the linearized plasmid pUC-hNF114. T4 DNA ligase and ligation buffer were added, and the mixture incubated overnight at 15° C. The ligation was used to transform *E. coli* MC1061 to ampicillin resistance. One plasmid, designated pUC-hNF116, was shown to contain the substituted region, proANP*gln, by the DNA sequencing method of Sanger et al (supra).

Plasmid phNF86 digested with EcoRI and HindIII was then purified as a linear molecule from a 0.6% agarose gel and 50 ng mixed with at least 100 ng of EcoRI-HindIII proANP*gln fragment purified on a 0.6% agarose gel from an EcoRI and HindIII digest. Following overnight incubation with T4 DNA ligase and ligation buffer at 15° C., competent *E. coli* MC1061 were transformed to ampicillin resistance, grown overnight in culture, and plasmid DNA prepared. One expression vector, designated phNF117, encoded the new proANP*gln gene fused to the β-gal-(thr)6 leader peptide. *E. coli* W3110 carrying this plasmid was shown to express the hybrid protein in shake flask cultures, upon the addition of 3-β-indoleacrylic acid; densitometer tracings of Coomassie blue-stained SDS polyacrylamide gels estimated the hybrid protein at 10% of total cell protein.

(e) Construction of plasmid phNF120-1

Plasmid phNF120-1 is identical to phNF117, except that the Glu appearing in the β-gal-(thr)6 leader is altered to Gln, thus leaving only one Staph V8 cleavage site in the expression product. The plasmid was constructed site-directed mutagenesis of phNF117, and the product confirmed to have the sequence shown in FIG. 2.

(f) Construction of plasmid phNF120-3

Plasmid phNF120-3 is identical to phNF120-1, except that the expression product does not contain any Staph V8 cleavage sites.

EXAMPLE 2

Purification of recombinant human ANP-fusion protein

Fermentation

E. coli W3110 cells transformed with phNF117 were fermented by a fed-batch fermentation process in complex media containing an initial concentration of 5.0 g/L glucose. A concentrated glucose feed was started when the residual sugar was measured to be less than 0.5 g/L. The feed rate was then adjusted to maintain a residual glucose concentration of less than 1.0 g/L and a minimum dissolved oxygen of 20%. Fusion protein production was induced by the addition of 100 mg/L indole-acrylic acid (IAA) when the cell density was 40.0 $OD_{590}$. The fermentation was continued for an additional 14.5 h and harvested at a cell density of 73.0 $OD_{590}$. The total fermentation time was about 28.5 h.

Cell Recovery

Eighteen liters of fermentation broth were divided into six 1liter bottles and centrifuged at 5,000 rpm for 30 min at 4° C. in a Sorvall RC-3B centrifuge. The supernatant was discarded, and the bottles refilled with whole fermentation broth and centrifuged again. This process was repeated three times, resulting in a recovery of 1.23 Kg cells (wet weight). All cells were frozen at −85° C. until further processing. We have also used a cross-flow microfiltration unit equipped with 0.1 μm membranes (Sartorius, Inc., Yauco, P.R.) to reduce the fermentation broth volume so that only one centrifugation step is required to recover the cells.

Homogenization

Two hundred grams of cells were thawed to 4° C. and suspended in 2 liters (1:10, w/v) of 0.01M MES (2-[N-morpholino]ethanesulfonic acid), pH 6.0, for 1 hr at 4° C. The cell suspension was recirculated 3 times at 300 mL/min, with cooling, through a Microfluidizer (Model 110Y, Microfluidics corp., Newton, MA) operated at 10,000 psi. The fluidizer was equipped with 75- and 150-micron mixing chamber to break open the cells and release the intracellular proteins. Cell lysis was judged to be greater than 90% complete by microscopic examination.

The lysate was divided between 1 liter bottles and centrifuged at 5,000 rpm in a Sorvall RC-3B centrifuge for 30 min at 4° C. The pellet containing the insoluble ANP-fusion protein (inclusion bodies) was saved and the supernatant containing the soluble E. coli proteins was discarded.

Wash Inclusion Bodies

The lysate pellet (inclusion bodies) was resuspended in 750 mL (1:10, w/v) of 0.5M urea in 0.04M $H_2SO_4$ with magnetic mixing at 4° C. for 30 min. The suspended inclusion bodies were recirculated through the microfluidizer twice, to produce a homogeneous mixture and to break open any residual cells that may have copelleted with the inclusion bodies. The mixture was centrifuged at 5,000 rpm in a Sorvall RC-3B centrifuge at 4° C. for 20 min and the pellet saved. The washed pellet may be stored at −70° C. until further processing.

These inclusion bodies were washed with the low pH solution for two reasons: (1) to remove residual soluble proteins, and (2) to inhibit endogenous proteolytic enzymes that have been shown to digest ANP fusion protein at higher pH.

Solubilize Inclusion Bodies

The washed inclusion bodies were suspended in 0.5 L (1:5, w/v) of 6M urea in 0.4M $H_2SO_4$ with magnetic stirring at 4° C. for 30 min and then recirculated through the Microfluidizer twice to homogenize particles and solubilizes the ANP fusion protein. The resulting extract was centrifuged at 5,000 rpm in a Sorvall RC-3B rotor at 4° C. for 1 hr to remove residual insoluble materials. The supernatant may be processed immediately or stored at −70° C. to await further processing. Alternatively, the extract can be clarified by cross-flow filtration over a 0.2 μm filter, such as the Minitan unit (Millipore, Inc., Bedford, MA) with 500 $cm^2$ surface area.

Cation Exchange Chromatography

The new ANP fusion protein was shown to have a basic isoelectric point; therefore, cation exchange chromatography was selected to further purify the protein to near homogeneity before Staph V8 cleavage. A sample (0.5 L; 16.0 mg protein/mL) of solubilized ANP fusion protein was diluted to 4.0 L with 6M urea in 0.01M MES and the pH was adjusted to 6.0 with sodium hydroxide at 4° C. The diluted sample was loaded at 50 mL/min (38.2 cm/h linear velocity) onto a 10×16.5 cm (1.3 L) column of CM (carboxymethyl)-Sepharose ® Fast-Flow (Pharmacia, Inc., Piscataway, N.J.) equilibrated with 6M urea in 0.01M MES, pH 6.0 at 4° C. (Alternatively, one may employ sulfopropyl-Sepharose ® or other cation exchange materials.) After loading, unbound proteins were washed into the flow-through fraction with additional equilibration buffer until the absorbance at 280 nm returned to baseline. Fusion protein was then eluted with a solution of 6M urea, a linear gradient from 0 to 0.06M NaCl in 0.01M MES (or 0.06M NaCl in 0.01M MES), pH 6.0, at 100 mL/min (76.4 cm/hr linear velocity) and collected in 400 mL fractions. Fractions were analyzed for purity by SDS-PAGE before pooling for cleavage, and 2.7 g were recovered (34% step yield). It may be advantageous to use other pH values. A pH of 6.0 was used herein to minimize any carbamoylation reactions that may result from urea decomposition at elevated pH.

Cleavage with Staph V8

CM-Sepharose ® purified fusion protein was shown to contain trace levels of E. coli proteolytic enzymes which led to product loss and nonspecific fragmentation of the fusion during prolonged incubation with immobilized Staph V8. These nonspecific proteases were inactivated by heating the CM-purified fusion protein to 80° C. as follows. First, 0.1M Tris-$SO_4$, pH 9.0, is heated to 80° C. and mixed with an equal volume of purified fusion protein solution. The solution is maintained at 80° C. for 30 min, then cooled to room temperature. During this treatment, the urea concentration is reduced to 3M so that it will not inhibit the cleavage reaction. If necessary, the volume of this solution may be reduced, prior to cleavage, by ultrafiltration with 10,000 MWCO membranes.

Figure 7B:
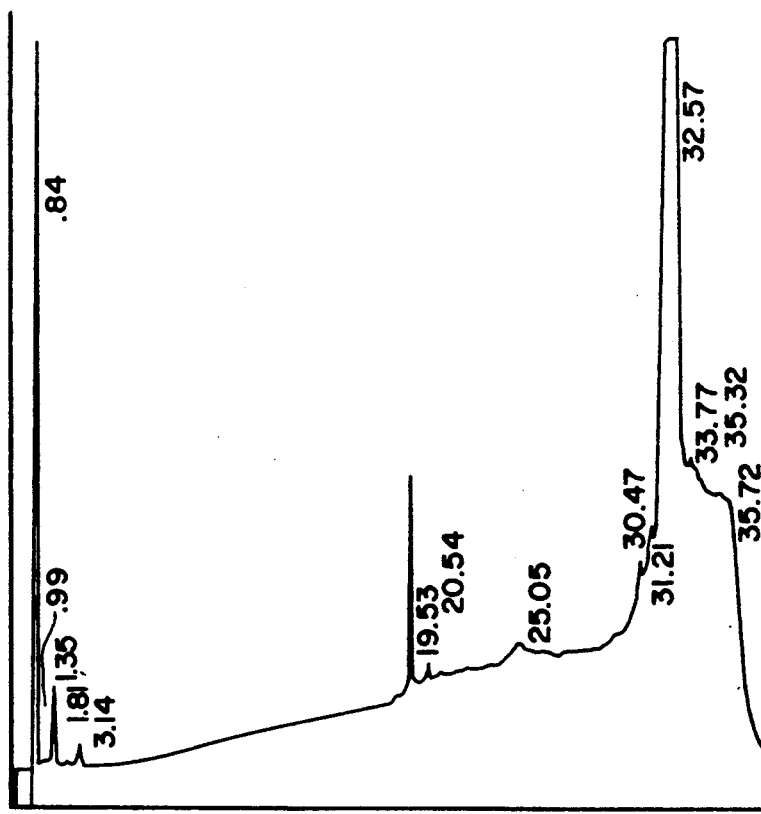
Figure 7C:
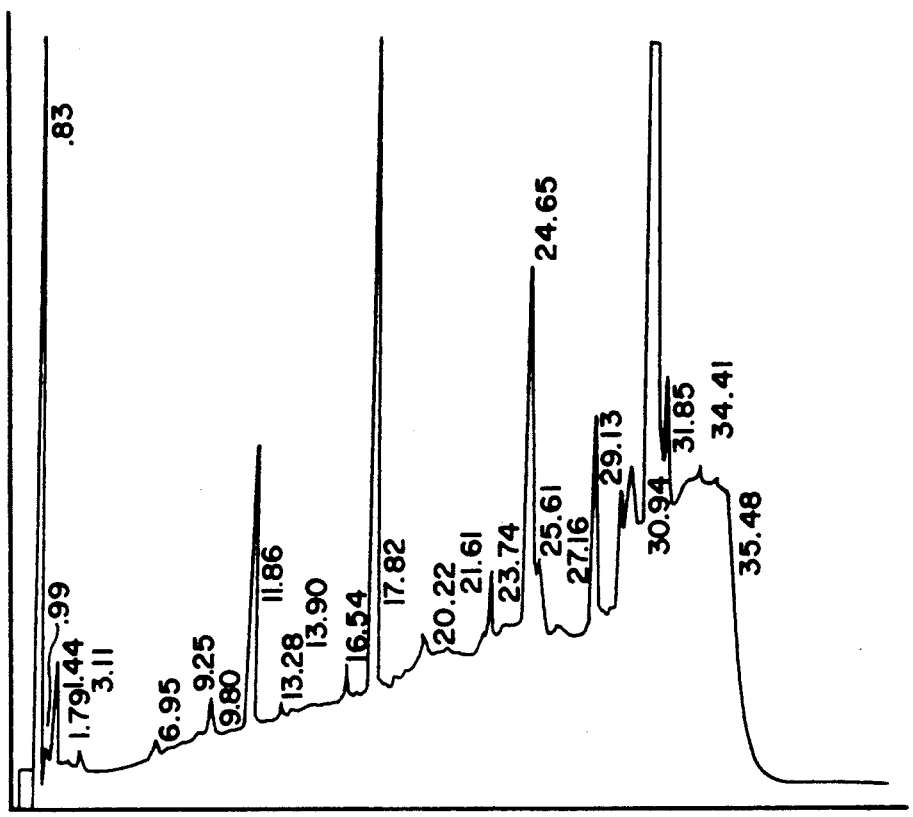
Figure 7D:
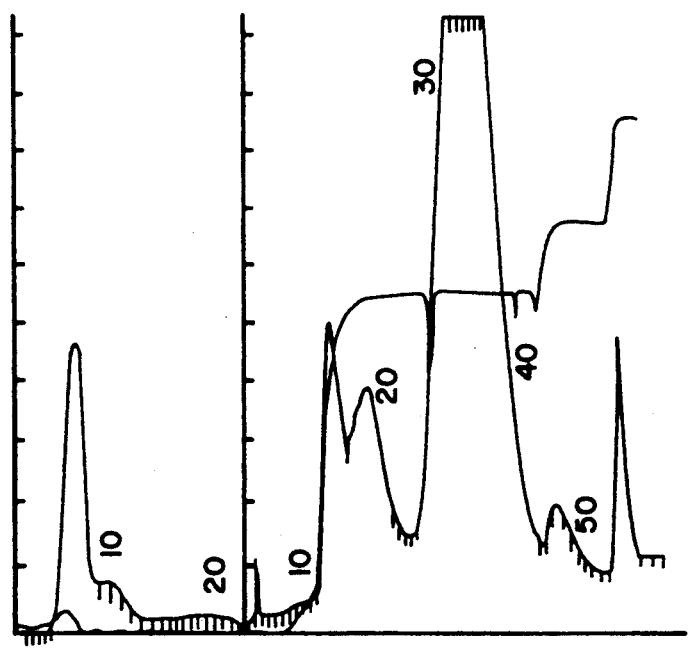
Figure 7E:
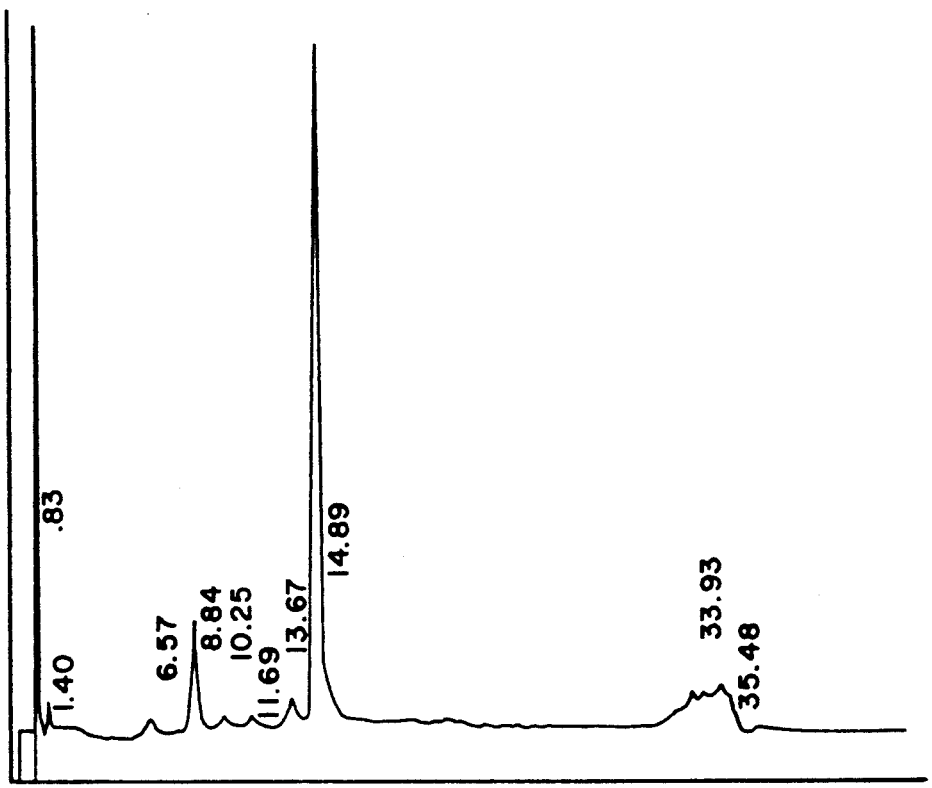
Figure 7F:
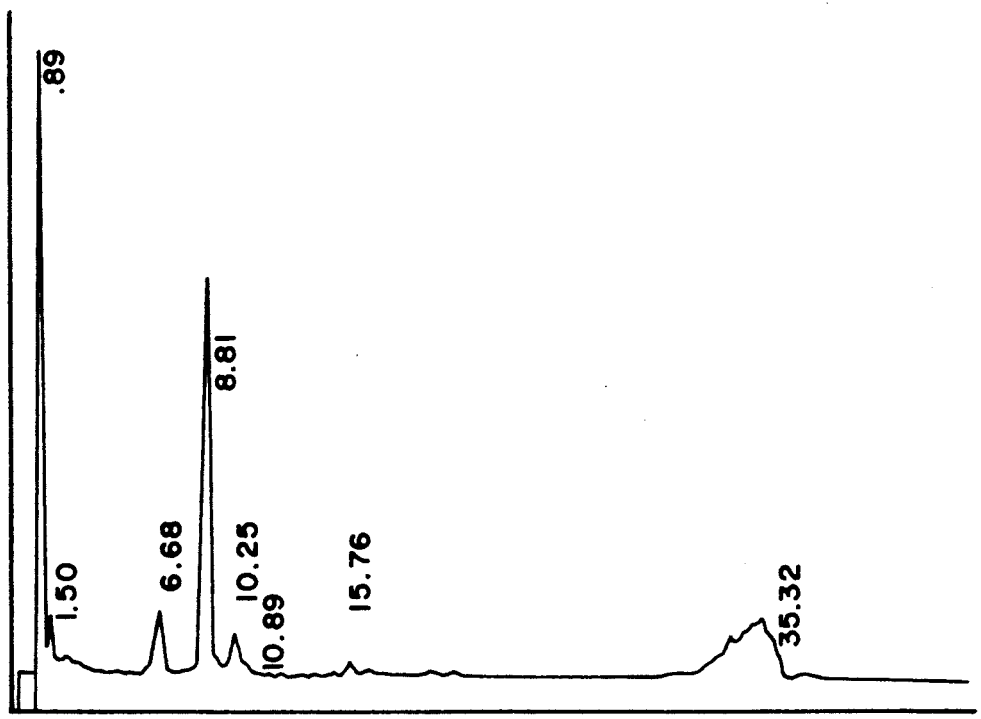
Figure 7G:
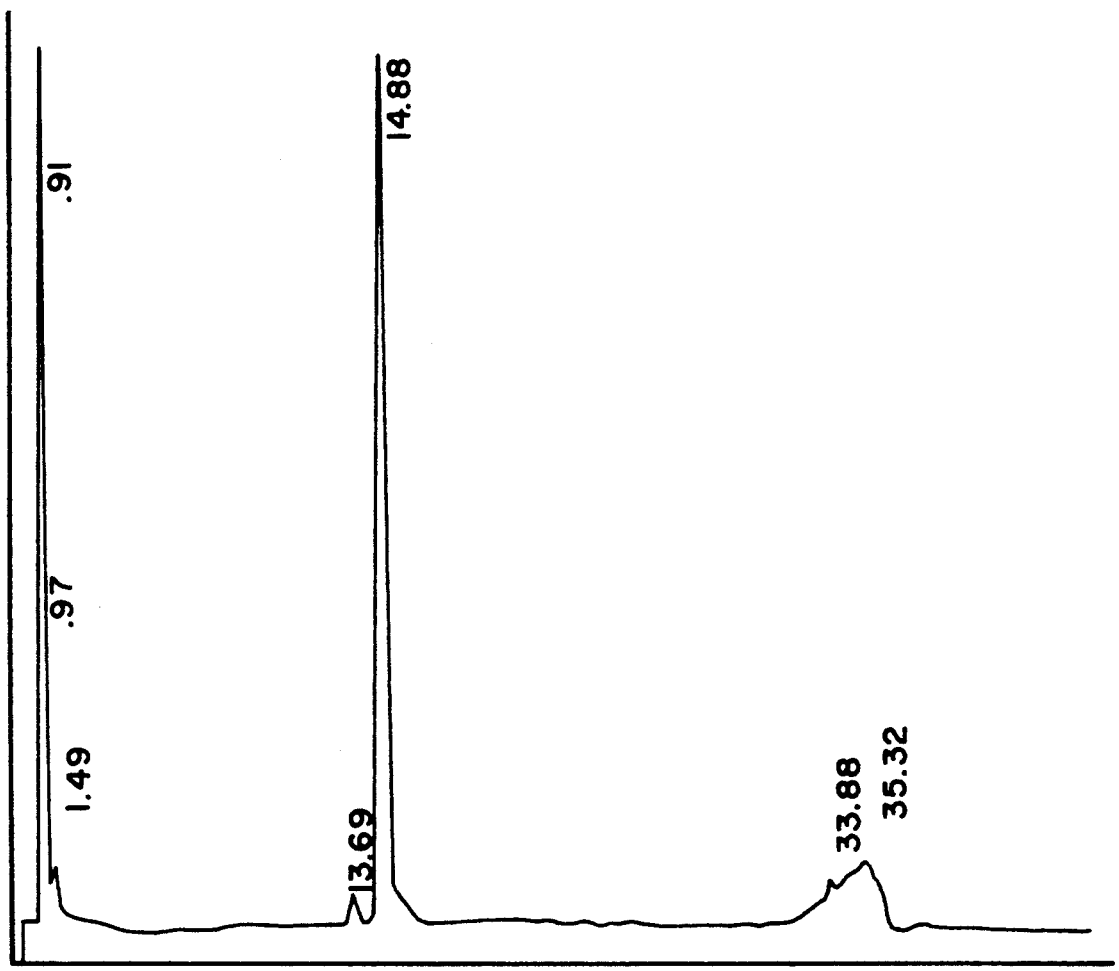

Staph V8 (endoproteinase Glu-C, Boehringer Mannheim GmbH, West Germany) was immobilized onto glutaraldehyde-activated PVC-silica composite membranes (Amerace, Inc., Hackettstown, N.J.) to a density of approximately 0.2 mg enzyme/cm$^2$ membrane. (One may alternatively employ cyanogen bromide-activated Sepharose ®, or other activated resins, membranes, or substrates.) Three 47 mm diameter membranes containing approximately 15 mg Staph V8 were connected in parallel and equilibrated with 0.05M Tris-SO$_4$, pH 9.0, at 2 mL/min at room temperature. Heat-treated fusion protein solution (200 mL) containing 1000 mg of protein was recirculated through the membrane system at 2 mL/min for 16 hr at room temperature. Cleavage was monitored by SDS-PAGE and RP-HPLC. FIG. 7A shows the RP-HPLC chromatogram of a sample prepared as described above, after purification on carboxymethyl Sepharose ®. FIG. 7B shows the RP-HPLC chromatogram of the sample after cleavage with Staph V8. One may alternatively effect cleavage using soluble (not immobilized) enzyme.

Ultrafiltration Size Separation

After cleavage with immobilized Staph V8, ANP was separated from the high molecular weight cleavage products by simple size separation. Ultrafiltration of the cleavage mixture over an Amicon YM10 membrane (10,000 MWCO) with washing, provided about 80% recovery of the product in the filtrate stream, free of high molecular weight fragments.

In addition to ANP, any ultrafiltration filtrate stream may contain the N-terminal peptide (when phNF117 is used), and urea from the cleavage reaction. The N-terminal peptide may be eliminated by replacing the β-gal-(thr)6 leader peptide with the Glu→Gln variant described above. To separate ANP from these substances, a second cation exchange chromatography step may be used. Alternatively, gel filtration chromatography can be used to separate ANP from high molecular weight cleavage products.

Cation Exchange Chromatography

Cation exchange chromatography was used to separate ANP from its cleavage products after cleavage or after ultrafiltration. In this step, ANP was chromatographically resolved on a CM-Sepharose ® Fast Flow column with a salt and pH gradient of ammonium acetate.

Alternatively, ANP has been separated by reversed-phase high performance liquid chromatography and lyophilized to remove organic solvents.

What is claimed is:

1. A method for producing a purified peptide, said method comprising:
   (a) expressing a gene encoding a fusion protein within a host cell, wherein said fusion protein comprises
      (i) a carrier protein of about 10 to about 50 kDa which does not contain Glu residues or Asp-Gly sequences as a Staph V8 cleavage site, wherein said carrier protein consists essentially of the sequence:

Asn—Pro—Met—Tyr—Asn—Ala—Val—Ser—Asn—Ala—Asp—
Leu—Met—Asp—Phe—Lys—Asn—Leu—Leu—Asp—His—Leu—
X$_1$—X$_2$—Lys—Met—Pro—Leu—X$_3$—Asp—X$_4$—Val—Val—Pro—
Pro—Gln—Val—Leu—Ser—X$_5$—Pro—Asn—X$_6$—X$_7$—Ala—
Gly—Ala—Ala—Leu—Ser—Pro—Leu—Pro—X$_8$—Val—Pro—
Pro—Trp—Thr—Gly—X$_9$—Val—Ser—Pro—Ala—Gln—Arg—
X$_{10}$—X$_{11}$—Gly—Ala—Leu—Gly—Arg—Gly—Pro—Trp—Asp—
Ser—Ser—Asp—Arg—Ser—Ala—Leu—Leu—Lys—Ser—Lys—
Leu—Arg—Ala—Leu—Leu—Thr—Ala—Pro—Arg—Ser—
Leu—Lys—Phe—;

wherein
   X$_{1-9}$ are each independently selected from the group consisting of Ala, Asp, Cys, Phe, Gly, His, Ile, Lys, Leu, Met, Asn, Pro, Gln, Arg, Ser, Thr, Val, Trp, and Tyr; and
   X$_{10}$ and X$_{11}$ are each independently selected from the group consisting of Ala, Arg, Asp, Cys, Phe, Gly, His, Ile, Lys, Leu, Met, Asn, Pro, Gln, Ser, Thr, Val, Trp, and Tyr, with the proviso that X$_{11}$ is not Asp, and if X$_{10}$ is Asp then X$_{11}$ is not Gly;
   (ii) a Staph V8 cleavage site positioned at the C-terminal of said carrier protein; and
   (iii) said peptide, not containing a Staph V8 cleavage site, fused to said cleavage site;
   wherein said fusion protein exhibits a pI of about 8.0 or greater;
   (b) separating said fusion protein from proteins endogenous to said host cell by a process, at least one step of which consists essentially of cation exchange chromatography under conditions wherein said fusion protein is adsorbed to a cation exchange column while proteins endogenous to said host cells are not adsorbed to said column;
   (c) eluting said fusion protein;
   (d) cleaving said fusion protein at said cleavage site to liberate said carrier protein from said peptide; and
   (e) recovering said peptide free from said carrier protein.

2. The method of claim 1, wherein X$_{1-9}$ are each Gln.

3. The method of claim 2, wherein said fusion protein further comprises an N-terminal leader of about 6 to about 20 amino acids.

4. The method of claim 3, wherein said leader comprises about 3 to about 9 Thr residues.

5. The method of claim 4, wherein said leader consists essentially of the sequence:

Met—Thr—Met—Ile—Thr—Asn—Leu—Thr—Thr—Thr—Thr—Thr—Thr—Gln—Phe—Arg—Met—.

6. The method of claim 5, wherein said peptide is selected from the group consisting of ANP, brain natriuretic peptide, somatostatin, glucagon-like peptide, calcitonin, lung surfactant, insulin, growth hormone releasing factor, bradykinins, endorphins, and enkephalins.

7. The method of claim 6, wherein said peptide is human ANP or an analog of ANP.

8. The method of claim 7, wherein said peptide consists essentially of the sequence:

Arg—Ser—Ser—Cys—Phe—Gly—Gly—Arg—Met—Asp—Arg—Ile—Gly—Ala—Gln—Ser—
Gly—Leu—Gly—Cys—Asn—Ser—Phe—Arg—Tyr.

* * * * *